US012686845B2

(12) United States Patent
Pierson et al.

(10) Patent No.: US 12,686,845 B2
(45) Date of Patent: *Jul. 21, 2026

(54) APPARATUS AND PROCESS FOR THE AUTOMATED MANUFACTURING OF GENETICALLY ENGINEERED CELLS FROM BIOLOGICAL FLUIDS

(71) Applicant: LIMULA SA, La Tour-de-Peilz (CH)

(72) Inventors: Yann Pierson, La Tour-de-Peilz (CH); Carmelo Bisognano, Geneva (CH)

(73) Assignee: LIMULA SA, La Tour-de-Peilz (CH)

( * ) Notice: Subject to any disclaimer, the term of this patent is extended or adjusted under 35 U.S.C. 154(b) by 15 days.

This patent is subject to a terminal disclaimer.

(21) Appl. No.: 18/791,762

(22) Filed: Aug. 1, 2024

(65) Prior Publication Data

US 2024/0392230 A1 Nov. 28, 2024

Related U.S. Application Data

(62) Division of application No. 16/972,935, filed as application No. PCT/EP2019/064507 on Jun. 4, 2019, now Pat. No. 12,077,745.

(30) Foreign Application Priority Data

Jun. 6, 2018 (EP) ..................................... 18176314

(51) Int. Cl.
*B04B 5/04* (2006.01)
*B01L 3/00* (2006.01)
(Continued)

(52) U.S. Cl.
CPC ........... *C12M 41/48* (2013.01); *B01L 3/5021* (2013.01); *B04B 5/0421* (2013.01); *C12M 23/14* (2013.01); *C12M 23/50* (2013.01); *C12M 47/02* (2013.01)

(58) Field of Classification Search
CPC ...... C12M 41/48; C12M 23/14; C12M 23/50; C12M 47/02; C12M 23/02; C12M 41/44;
(Continued)

(56) References Cited

U.S. PATENT DOCUMENTS 109,658 A * 11/1870 Phillips
2,009,690 A * 7/1935 Flowers ................ B01L 3/5021
422/918
(Continued)

FOREIGN PATENT DOCUMENTS

GB 2349108 A * 10/2000 ............... B04B 5/02
WO WO-2004039471 A1 * 5/2004 ........... B04B 5/0421
(Continued)

OTHER PUBLICATIONS

Jun. 27, 2019 Search Report issued in International Patent Application No. PCT/EP2019/064507.
Jun. 27, 2019 Written Opinion issued in International Patent Application No. PCT/EP2019/064507.

*Primary Examiner* — Charles Cooley
(74) *Attorney, Agent, or Firm* — Oliff PLC

(57) ABSTRACT

An automated apparatus suitable for the preparation of genetically transformed cells from biological fluids including of an operating unit and a rotating concentric hollow processing chamber able to automatically process biological samples, such as white blood cells from apheresis, bone marrow or cultured cells, to manufacture genetically engineered cells. The operating unit is rotatable around its center about a horizontal axis and the processing chamber is rotatable about its central rotor axis perpendicular with the rotating axis of the operating unit. The processing chamber can be operated at high rotating speeds when oriented vertically to generate centrifugal force on the contained sample allowing separation of solids from liquids and at low speeds or by series of fast sequential clockwise and coun- (Continued)

terclockwise rotations when oriented horizontally for incubation, solid resuspension and magnetic beads magnetic attachment.

13 Claims, 7 Drawing Sheets

(51) Int. Cl.
  C12M 1/00            (2006.01)
  C12M 1/36            (2006.01)

(58) Field of Classification Search
  CPC . C12M 41/46; B04B 5/00; B04B 5/02; B04B
              5/04; B04B 5/0407; B04B 7/08; B04B
                  5/0421; B04B 5/0414; B01L 3/5021
  USPC ............................... 494/16–21; 422/547–549
  See application file for complete search history.

(56)                    References Cited

U.S. PATENT DOCUMENTS

| | | | | |
|---|---|---|---|---|
| 2,616,619 | A * | 11/1952 | Macleod | B04B 5/0442 |
| | | | | 209/208 |
| 2,928,591 | A * | 3/1960 | Deaver | B01L 3/5021 |
| | | | | 209/172 |
| 4,933,291 | A * | 6/1990 | Daiss | B01L 3/0275 |
| | | | | 356/244 |
| 2005/0054506 | A1* | 3/2005 | Bradley | C12M 33/10 |
| | | | | 494/31 |
| 2014/0206521 | A1* | 7/2014 | Hamandi | B04B 5/0421 |
| | | | | 494/37 |
| 2017/0218331 | A1 | 8/2017 | Miltenyi et al. | |
| 2021/0246413 | A1* | 8/2021 | Pierson | C12M 41/48 |

FOREIGN PATENT DOCUMENTS

| | | | |
|---|---|---|---|
| WO | 2009/072003 | A2 | 6/2009 |
| WO | 2016/118780 | A1 | 7/2016 |

* cited by examiner

15

9

8

1

19

11

10

14

13

87

9

1

2

11

80

19

88

89

92

95

18

91

90

16

17

96

70

72

71

73

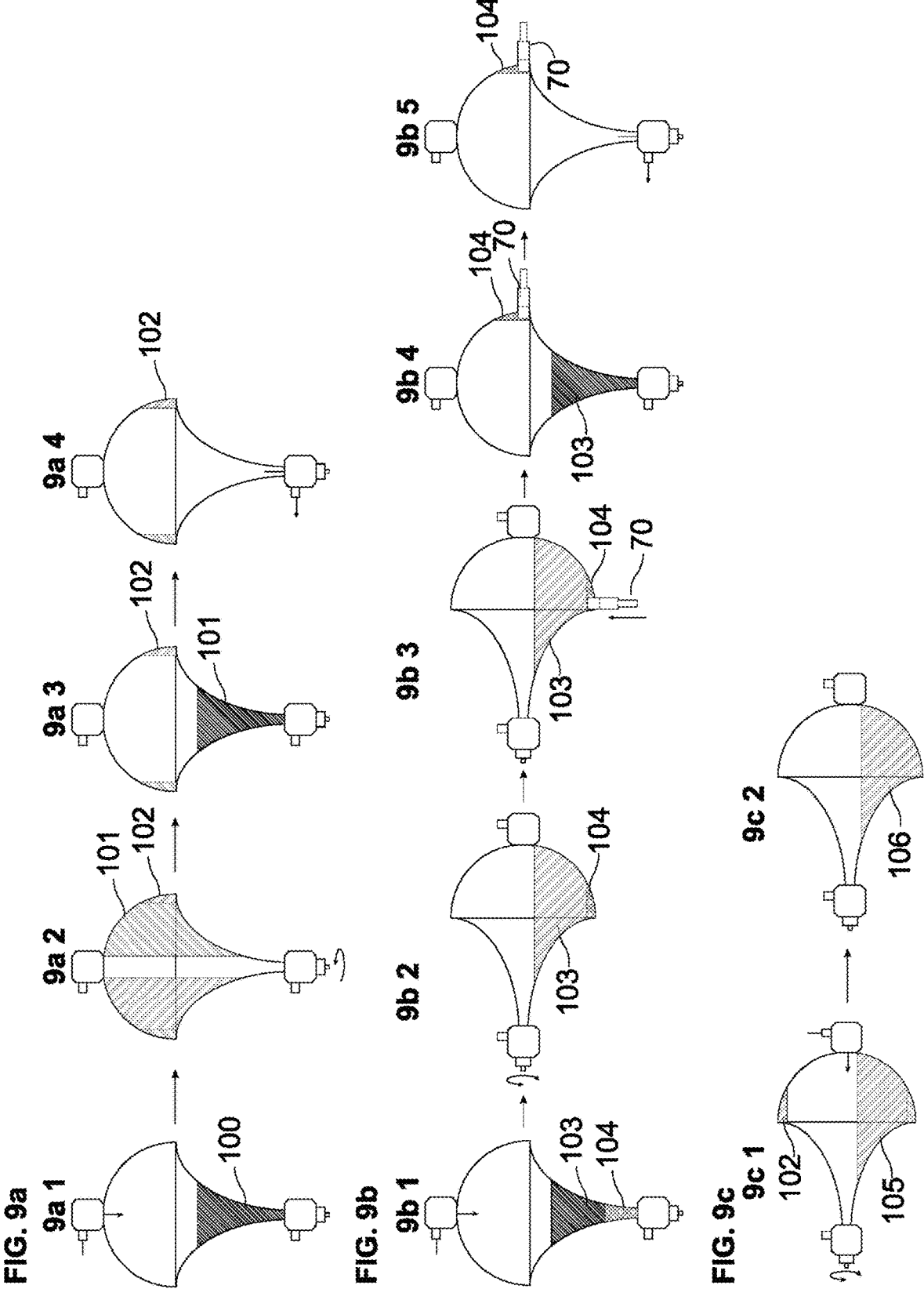

APPARATUS AND PROCESS FOR THE AUTOMATED MANUFACTURING OF GENETICALLY ENGINEERED CELLS FROM BIOLOGICAL FLUIDS

This application is a Divisional application of U.S. patent application Ser. No. 16/972,935 filed Dec. 7, 2020, which is a U.S. National Phase of PCT/EP2019/064507 filed Jun. 4, 2019, which claims priority to European Application No. 18176314.5 filed Jun. 6, 2018, which are incorporated herein by reference in their entirety.

FIELD OF THE INVENTION

The invention relates to an automated apparatus and process for the manufacturing of genetically engineered cells from biological fluids. In particular the apparatus allows for the preparation of therapeutic solutions and biological fluid processing by genetically engineering cells, separating cells from fluids and cell washing, concentrating and dilution through the application of physical treatment to biological fluids, such as centrifugation, magnetic separation and fluid mixing in the context of gene-therapy related products.

BACKGROUND OF THE INVENTION

Gene-therapy, based on stem cell or chimeric antigen receptor T-cells genetic engineering, is currently used on patients and offer unprecedented results against several forms of cancer. The therapeutic product is generally manufactured as follows: Collection of white blood cells from patient body fluids is performed. From this collection a subset of cells of interest have to be washed and isolated. These relatively few isolated cells, will be genetically modified by the action of a viral vector. The modified cells have to be expanded back to a large culture. The manufacturing of these therapies is generally performed by human technicians in clean rooms and is subject to strict standard operating procedures. Human labor negatively impacts the quality and reproducibility of the final therapeutic product and automation should be applied to increase the success of producing an applicable therapeutic product.

WO 2009/072003 A2 (MILTENYI BIOTEC GMBH [DE]; MILTENYI STEFAN [DE]; SCHIMMELPFENNIG WINFRIED) discloses a system, comprising: a) a sample processing unit, comprising an input port and an output port coupled to a rotating container having at least one sample chamber, the sample processing unit configured provide a first processing step to a sample or to rotate the container so as to apply a centrifugal force to a sample deposited in the chamber and separate at least a first component and a second component of the deposited sample; and b) a sample separation unit coupled to the output port of the sample processing unit, the cell separation unit comprising separation column holder, a pump and a plurality of valves configured to at least partially control fluid flow through a fluid circuitry and a separation column positioned in the holder, the separation column configured to separate labeled and unlabeled components of sample flowed through the column.

In US 2017/218331 A1 (MILTENYI STEFAN [DE] ET AL) it is disclosed a cell modification device, comprising a centrifugation chamber with at least one cell modifying surface with a normal vector having an angle of 135-45° to the rotational axis of the centrifugation chamber, wherein the centrifugation chamber comprises at least one input/output port and the cells to be modified are immobilized at the cell modifying surfaces by the rotation of the centrifugation chamber at 2 to 2000 g. Furthermore, the invention relates to a method for modifying cells comprising the steps-introducing cells in a cell modification device, comprising a centrifugation chamber with at least one cell modifying surface with a normal vector having an angle of 135-45° to the rotational axis of the centrifugation chamber wherein and comprising at least one input/output port, —immobilizing the cells on the cell modifying surfaces by the rotation of the centrifugation chamber at 2 to 2000 g—maintaining the rotation of the rotation of the centrifugation chamber until the cells are modified.

In WO 2016/118700 A1 (HUTCHINSON FRED CANCER RES [US]) a platform for ex vivo isolation, production, and formulation of genetically-modified cells is described. The platform utilizes a software-enabled point-of-care and/or portable device making gene therapy more widely available.

US 2005/054506 A1 (BRADLEY BRUCE J [US]) describes a centrifuge separation chamber of particular use for separating microbes. The chamber has an upwardly flared conical shape, and a sample collecting groove at its widest point. Sample is collected in the sample groove as the chamber spins. When slowed to a stop, the supernatant sinks to the bottom of the chamber, leaving the sample in the sample groove where it can be easily accessed.

WO 2016/097889 A1 (BIOSAFE SA [CH]) discloses a process for the sequential processing of opaque and transparent biological fluids such as whole blood, apheresis blood, bone marrow blood, umbilical cord blood, buffy coat or cultured cells by processing steps in a hollow cylindrical centrifugal processing chamber (300) which is part of a disposable set. At least three different procedures selected from washing, incubation, transduction, separation, density gradient separation, dilution and volume adjustment are each carried out once or repeated a number of times according to a given processing profile in the processing chamber. Each procedure involves an input into the processing chamber, an operation in the processing chamber and an output from the processing chamber by displacement of a piston (310). The at least three different procedures are sequentially chained one after the other to constitute an overall sequential operation in the processing chamber and its disposable set. A first application is incubation for binding magnetic beads with human blood cells or stem cells. A second application is transduction by which foreign genetic material is inserted into human blood cells or stem cells by a virus. A third application is reconditioning biological fluids to achieve reproducible concentration and volumes of blood cells or stem cells.

As reported, efforts have already been made to automate the manufacture of genetically engineered cells. However, state of the art technologies such as those exemplified in WO 2016/097889 A1 or WO 2009/072003 A2 cannot currently perform the whole genetically engineered cell manufacturing in a single processing chamber. Difficulties reside in the variation of culture size along the process and parts of the process, such as respectively cell isolation or final cell expansion to the final desired cell number or cell isolation, have to be performed in another device increasing the process complexity and potential spoilage of the final product.

BRIEF DESCRIPTION OF THE INVENTION

One of the objects of the present invention is to provide an automated apparatus suitable for the preparation of genetically transformed cells. This apparatus is composed of an operating unit and a rotating concentric hollow processing chamber suitable for performing cell processing. The operating unit shape is hexagonal and able to rotate around a shaft which passes by its center and is perpendicular to the axis of rotation of the rotating concentric hollow processing chamber. The operating unit accommodates the rotating concentric hollow processing chamber and via its rotation can orient the processing chamber in different positions conferring different possible operations to said processing chamber. The operating unit possesses different functions on its six faces and possesses on one face a housing that holds the rotating concentric hollow processing chamber, can temperate the chamber and is equipped with an actionable magnetic array. Finally, the actionable magnetic array can closely fit the edge of the concentric hollow processing chamber to exert a magnetic field in the chamber. The rotating hollow processing chamber can by performing centrifugation when oriented vertically separate solids from a liquid and can, when oriented horizontally, perform solid resuspension and solution incubation. The rotating concentric hollow processing chamber is characteristic in its shape and is composed of a top part that is a half sphere with the round part facing up with a hole at the very top; and at the edges of the half sphere forming a perpendicular angle with the sphere, positioned between a quarter and halfway of the total height of the rotating concentric processing chamber, the bottom part begins, narrowing down into a funnel shape that follows a concave arched curve with a second hole at the very bottom. The rotating concentric hollow processing chamber is fitted with an inlet stator at the top and an outlet stator at the bottom allowing liquids to be pumped in and out of the chamber. Furthermore, the rotating concentric hollow processing chamber is connected at both its bottom and top stators to two independent sets composed of a disposable peristaltic pump head connected to a disposable multiple-way rotary selector valve head connected to several reagent or product pouches which forms a single use disposable kit. Finally, the rotating concentric hollow processing chamber possesses an actionable plug shaped to fit its bottom hole. It can be engaged or disengaged by means of an actuator to respectively block and unblock the processing chamber liquid outlet.

Another object of the invention is to provide a process herein defined as a set of operations performed via the operating unit and the rotating concentric hollow processing chamber such as filling the processing chamber, emptying the processing chamber, centrifugation to separate solids from liquids, aggregate resuspension, cell and/or reagents incubation, cell culture expansion, magnetic separation and volume adjustment allowing to perform the manufacturing process of genetically engineered cells.

Other objects and advantages of the invention will become apparent to those skilled in the art from a review of the ensuing detailed description, which proceeds with reference to the following illustrative drawings, and the attendant claims.

BRIEF DESCRIPTION OF THE DRAWINGS

The apparatus and processes are described by means of technical drawings wherein:

FIG. 9a is a flow diagram of a biological solid separation operation.

FIG. 9b is a flow diagram of a magnetic separation of cells of interest operation.

FIG. 9c is a flow diagram of an aggregate resuspension operation and a reagents and/or cells incubation operation.

DETAILED DESCRIPTION OF THE INVENTION

Figure 1:
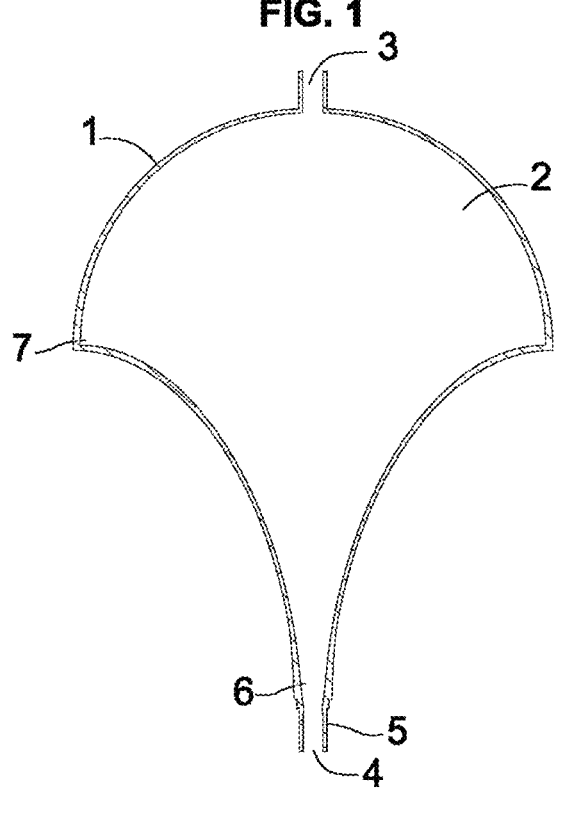
FIG. 1 depicts a cross-sectional view of the rotating concentric hollow processing chamber.

Although methods and materials similar or equivalent to those described herein can be used in the practice or testing of the present invention, suitable methods and materials are described below. All publications, patent applications, patents, and other references mentioned herein are incorporated by reference in their entirety. The publications and applications discussed herein are provided solely for their disclosure prior to the filing date of the present application. Nothing herein is to be construed as an admission that the present invention is not entitled to antedate such publication by virtue of prior invention. In addition, the materials, methods, and examples are illustrative only and are not intended to be limiting.

In the case of conflict, the present specification, including definitions, will control.

Unless defined otherwise, all technical and scientific terms used herein have the same meaning as is commonly understood by one of skill in art to which the subject matter herein belongs. As used herein, the following definitions are supplied in order to facilitate the understanding of the present invention.

The term "comprise" is generally used in the sense of include, that is to say permitting the presence of one or more features or components.

As used in the specification and claims, the singular forms "a", "an" and "the" include plural references unless the context clearly dictates otherwise.

As used herein the term, processing chamber, without or preceded with any combination of the terms rotating, concentric and hollow refers to the same object.

As used herein the term, plug or actionable plug, refers to a stopper with the purpose of obstructing the flow of a liquid.

As used herein the terms, low speed rotation, is a rotation speed between 2 to 100 rpm; centrifugation is a rotation speed generating between 2000 to 6000 G; and fast sequential clockwise and counterclockwise rotations, are rotations between 2 to 400 rpm for between 1 to 10 s.

As used herein the term, sufficient time, when referring to cell expansion is between 12 to 24 hours; 2 to 20 minutes when referring to solid resuspension; 2 to 30 minutes when referring to centrifugation; 15 min to 8 hours when referring to lentiviral incubation.

As used herein the term, temperature compatible with cell culture standard, is between 32 to 38° C. when referring to cell culture expansion or incubation.

As used herein the term, satisfactory cell count, refers to a number of cells between $10^8$ and $10^{10}$ cells or more.

One object of the present invention is to provide an automated apparatus suitable or adapted for the preparation of genetically transformed cells from biological fluids comprising:

(i) an operating unit (80) that is rotatable around its center about a horizontal axis (19), (ii) a central axis shaft (16) holding the operating unit (80) providing support and electrical power, in which the operating unit (80) comprises a rotating concentric hollow processing chamber (1) having:

a top part that is a half sphere with the round part facing up with a protruding hole (3) at its very top;

bottom edges (7) of the half sphere positioned between a quarter and halfway of the total height of the rotating concentric processing chamber (1) forming a perpendicular angle with the bottom part of the concentric hollow processing chamber (1) which narrows down into a funnel shape (6) that follows a concave arched curve with a bottom hole (4) at its very bottom;

and wherein said operating unit (80) is configured to shift said rotating concentric hollow processing chamber (1) from a vertical (14) to a horizontal position (15) conferring different operations to said automated apparatus.

Preferably, the rotating concentric processing chamber (1) further comprises one or more side hole (5) circularly arranged above the bottom hole (4).

In one embodiment of the invention, the rotating concentric hollow processing chamber (1) is fitted with an inlet stator (8) at its top and an outlet stator (10) at its bottom allowing liquids to be pumped in and out of the rotating concentric hollow processing chamber (1).

In particular, an actionable plug (13) shaped to fit the bottom hole (4) of the rotating concentric hollow processing chamber (1) can be engaged (32) or disengaged (34) to respectively block or unblock the one or more circularly arranged side hole (5).

In one preferred embodiment, the rotating concentric hollow processing chamber (1) is connected at both its bottom (10) and top stators (8) to two independent sets composed of a disposable peristaltic pump head (58, 60) connected to a disposable multiple-way rotary selector valve head (57, 61) connected to several reagent or product pouches so as to form a disposable kit (66).

Preferably, the operating unit (80) is shaped as an hexagonal prism (96) that possesses different functions for each of the six operating unit faces (87, 88, 89, 91, 92, 95) and that can accommodate the rotating concentric hollow processing chamber (1) in a rotor housing (95) on one of the faces.

According to a preferred embodiment of the invention, the six operating unit faces (87, 88, 89, 91, 92, 95) of the operating unit (80) comprise;

two faces that are chambers engineered for the storage of liquid bags that can be temperature controlled (87, 89);

one face which is a rotor housing chamber (95) that holds the rotating concentric hollow processing chamber (1) and is equipped with an actionable magnetic array (70);

one face (91) that comprises a user interface (86) as well as attachment points for a peristaltic pump head (58) and multiple-way rotary selector valve head (57);

one face (92) that comprises attachment points for a peristaltic pump head (60) and multiple-way rotary selector valve head (61) and, one face (88) that contains data input/output connectors, power connectors as well as venting for temperature control.

Preferably, the actionable magnetic array (70) consists in an arched shape designed to fit the edge (7) of the rotating concentric hollow processing chamber (1) when engaged and further comprising one or more high magnetic field strength magnets (73) such as high magnetic field strength neodymium magnets.

Figure 3:
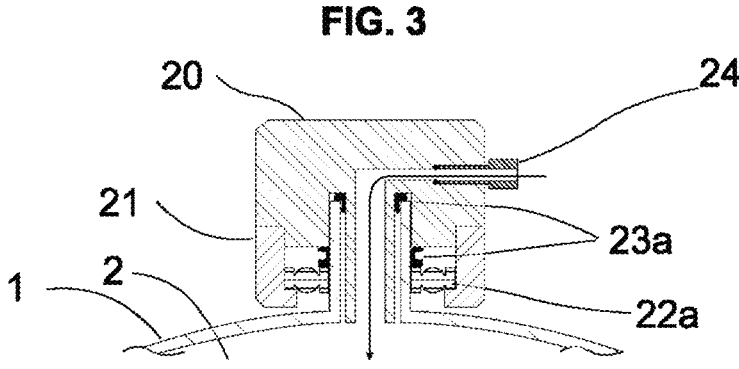
FIG. 3 is a focused cross-sectional view of the inlet stator.
Figure 4:
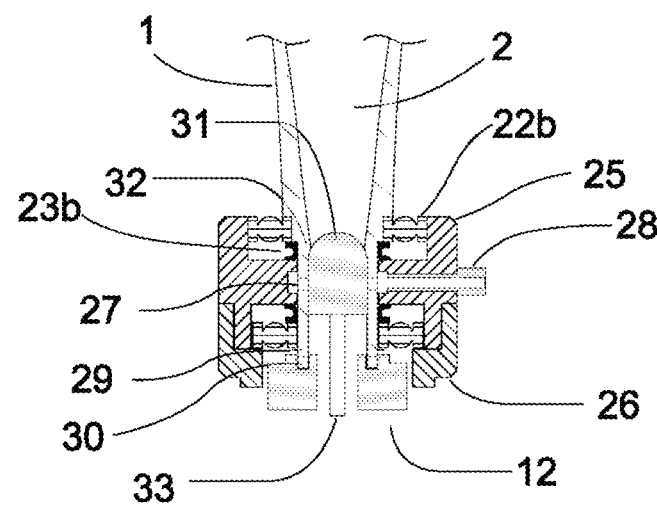
FIG. 4 is a focused cross-sectional view of outlet stator and its functional modes.
Figure 4:
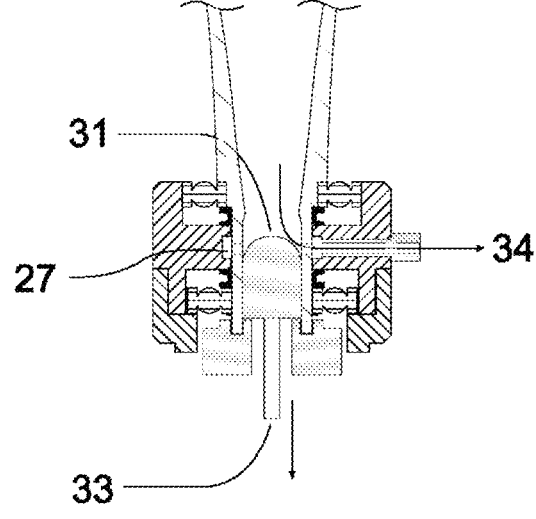
Figures 5, 6:
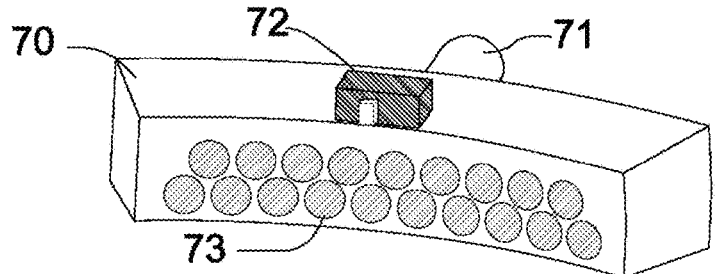
FIG. 5 is a schematic illustration of the rotation and movement range of the rotating concentric hollow processing chamber when mounted on the operating unit.
FIG. 6 is a perspective illustration of the actionable magnetic array.
Figure 7:
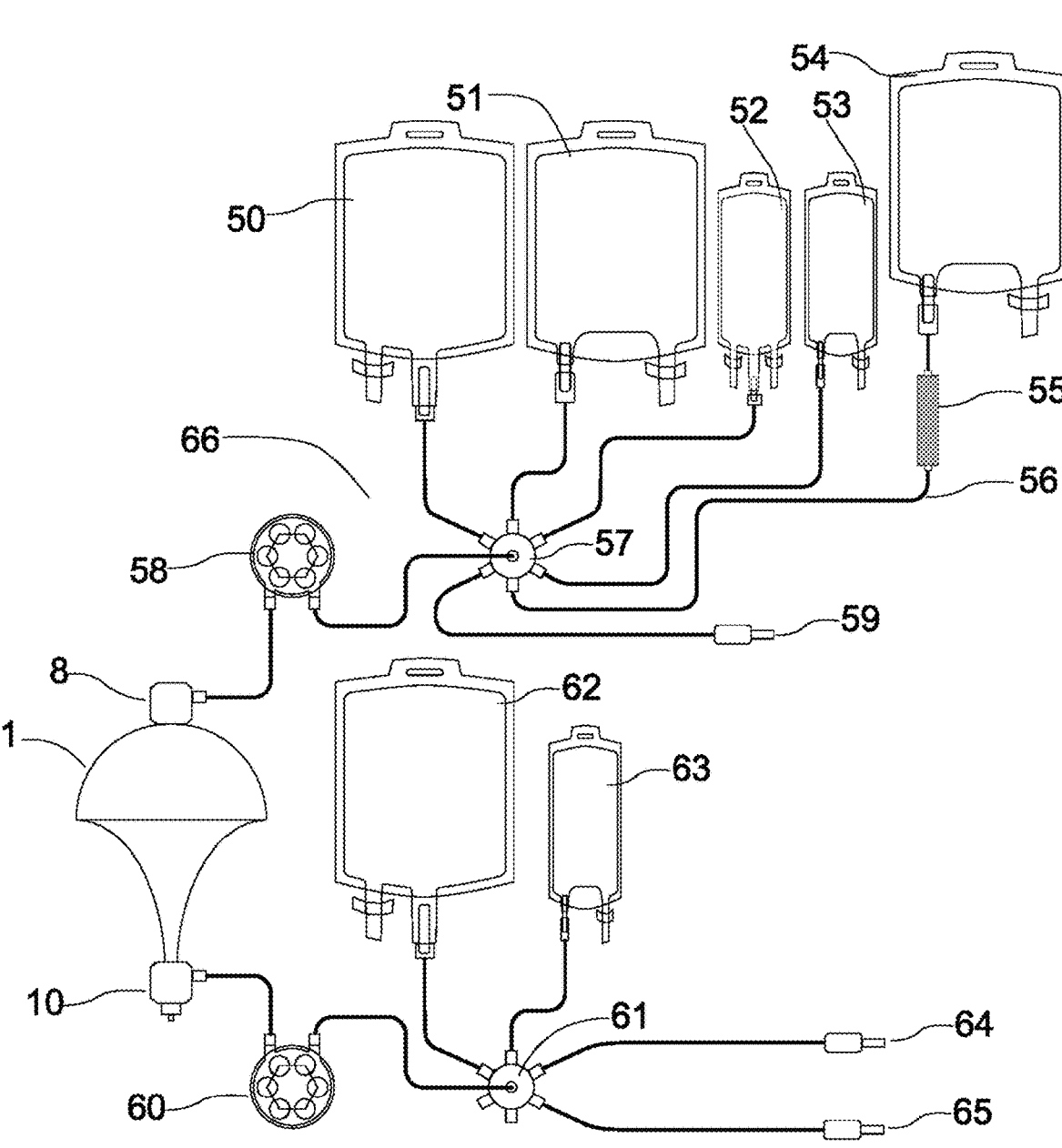
FIG. 7 is a scheme of the disposable kit used and its associated reagents.
Figure 8:
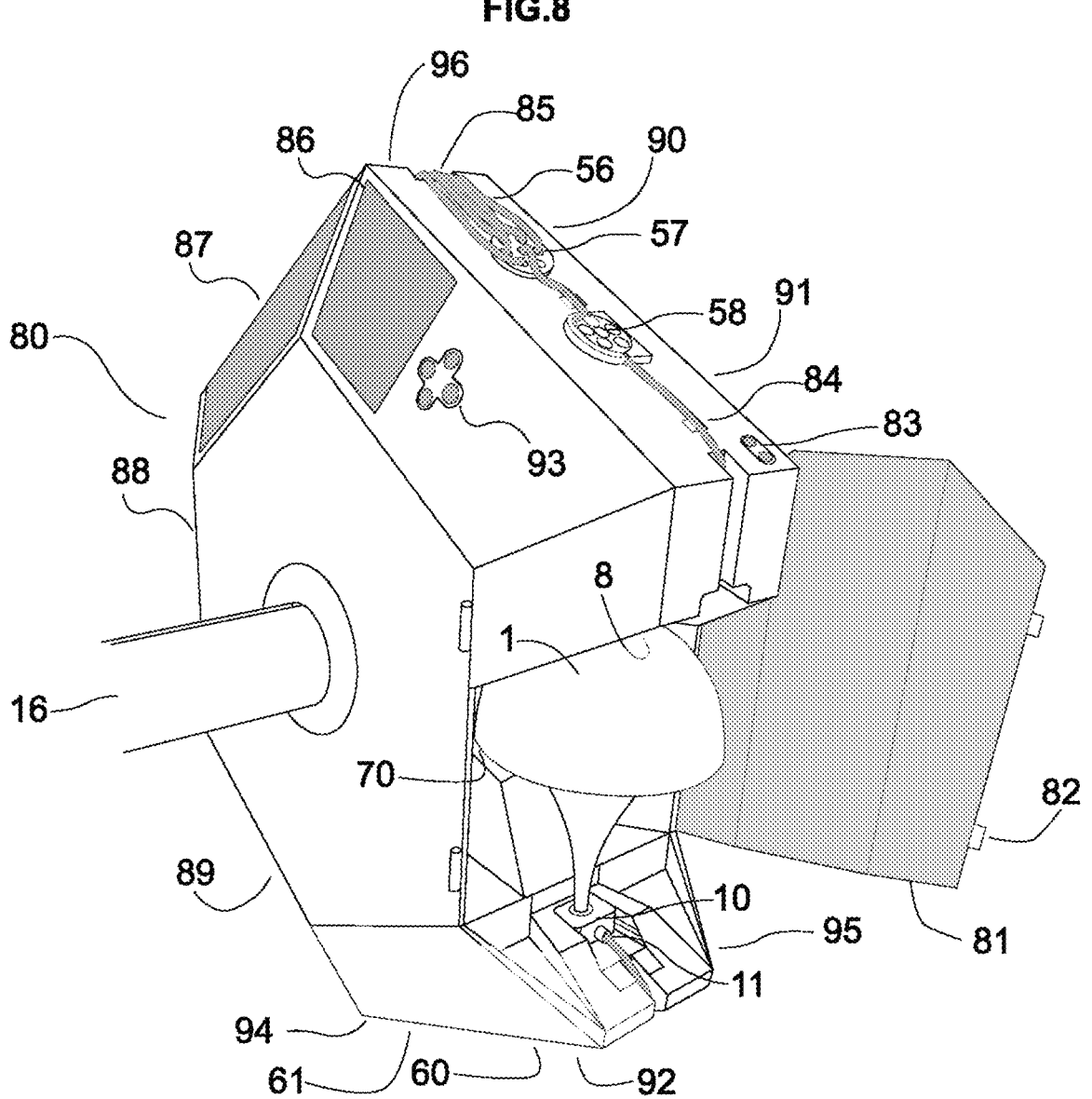
FIG. 8 is a perspective illustration of the operating unit mounted with a disposable kit.

In particular, the invention relates to an apparatus composed of two main parts: (i) an operating unit (FIG. 8) that is rotatable around its center about a horizontal axis and is held by a shaft that provides support and electrical power and (ii) a rotating concentric hollow processing chamber (FIG. 1) that is installed on said operating unit. The invention, by way of its operating unit acting on the rotating concentric hollow processing chamber, can process, in an automated fashion, biological samples, such as white blood cells from apheresis, bone marrow or cultured cells, to manufacture genetically engineered cells. The rotating concentric hollow processing chamber is fitted with an inlet stator (FIG. 3) and an outlet stator (FIG. 4) and is rotatable about its central rotor axis perpendicular with the rotating axis of the operating unit (FIG. 5). Said processing chamber can be operated at high rotating speeds when oriented vertically to generate centrifugal force on the contained sample and at low speeds or by series of fast sequential clockwise and counterclockwise rotations when oriented horizontally for incubation and solid resuspension (FIG. 9). The rotating concentric hollow processing chamber is connected at both its bottom and top stators to two independent sets composed of a disposable peristaltic pump head connected to a disposable multiple-way rotary selector valve head connected to several reagent or product pouches part of a disposable kit (FIG. 7).

Operating Unit

The operating unit (80) is an active system and is shaped as three hexagonal prisms joined at the bases (96). The central hexagonal prism is regular while the adjacent prisms possess outward bases that are smaller than their inward bases, which forms a tapering effect that makes the two sides of the device smaller than the central portion that is composed of the regular hexagonal prism. The operating unit (80) possesses different function for each of its six faces (87, 88, 89, 91, 92, 95) and can accommodate the rotating concentric hollow processing chamber (1) in a rotor housing (95) on one of the faces. The operating unit (80) is rotatable around its center about a horizontal axis (19) which passes through the shaft (16).

Figure 2:
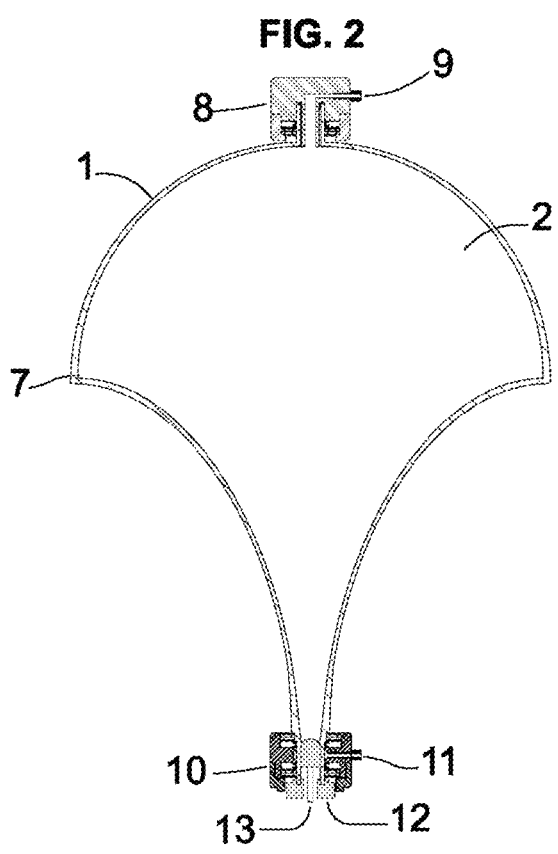
FIG. 2 depicts a cross-sectional view of the rotating concentric hollow processing chamber with its inlet and outlet stators.

The rotation of the operating unit (80) is performed by an electrical motor (17) located inside the operating unit (80) next to the central shaft (16). A second electrical motor (18), also located in the operating unit (80) drives the rotation of the rotating concentric hollow processing chamber (1). Both electrical motors (17, 18) are independent from each other, allowing for the innovative and advantageous feature that the rotation of the rotating concentric hollow processing chamber (1) can be operated in multiple orientations in space (FIG. 5). This feature allows for the utilization of the processing chamber (1) in a vertical position (14) to act as centrifugal body to separate solids from a suspension (FIG. 9a) and in a horizontal position (15) as incubator for cell culture expansion (FIG. 9c 2) or for solid resuspension in a solution (FIG. 9c). The orientation of the operating unit (80)

can be controlled by several buttons (83) conveniently located at the surface of the operating unit (80) faces. The operating unit (80) accommodates the disposable kit (66) by containing places on the six faces where the different elements of the kit can be installed.

On the top back face (87) resides a chamber for reagent storage. On the adjacent top front face (91) resides the user interface (86) as well as a means for attaching the inlet multiple-way rotary selector valve head (57) and the inlet disposable peristaltic pump head (58). On the adjacent front face, resides the rotor housing (95), for the rotating concentric hollow processing chamber (1) to be installed. On the adjacent bottom front face (92), resides means for attaching the outlet disposable peristaltic pump head (60) as well as the outlet multiple-way rotary selector valve head (61). On the adjacent bottom back face (89), resides a chamber for storing the waste (62), final products (63) and sampling port (64). On the back face (88), resides the input and output data transfer connectors as well as the secondary power connection and the thermal exchanger venting grids.

The rotating concentric hollow processing chamber (1) is installed in the rotor housing (95) by means of attachment points on the inlet stator (8) and outlet stator (10). The bottom outlet stator (10) of the processing chamber (1) is installed by clipping it to a rotating socket (12). The rotating concentric hollow processing chamber rotation (1) is rotated along its axis (14, 15) by this rotating socket (12) which is driven by an electrical motor (17). The top inlet stator (8) of the processing chamber (1) is installed by clipping it to the rotor housing (95). The actionable plug (13) that allows for the processing chamber outlet (5, 11) to be closed when the plug is engaged (32) is driven by a linear actuator that is installed in the rotor housing (95). Inside the rotor housing (95), at the back, resides the magnetic array (70) that can be brought near the processing chamber edge (7) by means of an actuator, applying a strong magnetic field to the inside of the processing chamber (1). This advantageous feature allows for the separation of magnetic beads (FIG. 8b) from a solution (103) inside of the processing chamber (1). The rotor housing (95) is closed with a transparent protective screen (81) held by attachments points (82). The rotor housing (95) space can be heated or cooled to temperatures compatible with cell culture standards by a set of thermal exchangers located in the back face (88) of the operating unit (80).

The magnetic array (70) is structurally shaped to closely fit to the rotating concentric hollow processing chamber (1), more precisely to the edge (7) between the top and bottom part of the processing chamber, when brought into contact. It is shaped as a ring segment or an arch and encompasses several high magnetic field strength magnets (73), such as but not limited to neodymium, all positioned close together with their central axis perpendicular to the rotating concentric hollow processing chamber (1) surface. A proximity sensor (72) is mounted on top of the body of the magnetic array (70) to evaluate the proximity of the magnetic array to the processing chamber surface (1). The magnetic array can be moved linearly via the action of a linear actuator on the shaft (71).

The top front face (91) allows for the installation of the inlet disposable peristaltic pump head (58) and the inlet disposable multiple-way rotary selector head (57). The bottom front face (92) allows for the installation of the outlet disposable peristaltic pump head (60) as well as the outlet multiple-way rotary selector valve head (61). Attachment points are designed for unambiguous kit installation with numbering and error-proof guides. The plastic tubing (56) is held to the surface by built-in clips (84) in a clear and orderly fashion for unambiguous system setup. A user interface screen (86) and a screen displaying the system and process status (90), located on the top front face, are operated via a four-way directional pad (93) and a keypad. The program for the operating unit (80) can be set by the operator via the user interface (86), or via a remote terminal and the disposable kit (66) installation guidelines are provided on the process advancement panel (90).

The top back (87) and the bottom back faces (89) are two chambers that can be opened and closed to store the reagent bags and solutions. The two bag storage chambers are rack-shaped to accommodate several bags and several liters of solution. The reagent bags are locked in the chamber by means of straps as well as a transparent plastic cover, which is practical for visual inspection. All the tubing (56) can exit the chambers via ducts (85, 94), holding the tubing in an orderly fashion, to connect to the rest of the disposable kit (66). The chambers can be heated or cooled by a set of thermal exchangers located at the back face (88) of the operating unit (80).

The face containing connectors (88) is located at the back. It is equipped with input and output data connectors such as, but not limited to, USB, RS232 and RJ45, for remote apparatus control and firmware upgrades. Thermal exchangers and heaters venting grids as well as secondary power inlets are located on this face.

Disposable Kit

The single use disposable kits (66) are composed of a rotating concentric processing chamber (1), connected at both its inlet stator (8) and outlet stator (10) to two independent sets composed of a disposable peristaltic pump head (58,60) connected to a disposable multiple-way rotary selector valve head (57, 61). The multiple-way rotary selector valve can connected to several medical grade reagent pouches, medical grade empty plastic pouches for collection or sampling and connection tubing.

The reagents used with this kit are typically biological samples, such as white blood cells from apheresis, bone marrow or cultured cells; as well as buffers, such as cell culture compatible buffers, saline and ionic solutions; cell culture growth medium; viral solutions, such as dilutions of lentiviral vectors or RNA vectors; suspensions of activating beads, suspensions of binding magnetic beads and reagents for magnetic bead detachment.

To exemplify this, magnetic separatory beads can be used for, but are not limited to, the purification of CD34+, CD20+ and CD19+ cell types and which can then be modified by lentiviral vectors for the manufacturing of chimeric antigen receptor T-cells or hematopoietic stem cell based gene therapies.

In one embodiment, the kit reagents that are used consist of a patient biological sample bag (54) connected to a bead filtration unit (55), phosphate buffer bag (50), cell culture growth medium bag (51), a bag containing a suspension of magnetic beads (52), a bag containing a lentiviral vector solution (53) and an inlet pin (59) for the addition of an additional reagent bag. All are connected to a disposable multiple-way rotary selector valve head (57) via medical grade tubing (56) connected to a disposable peristaltic pump head (58) connected to the inlet stator (8) of the rotating concentric hollow processing chamber (1). A generally large waste bag (62), able to accommodate more than the total volume of liquid reagent a collection bag (63), a sampling port (64) and a bag connection port (65) are connected to an outlet multiple-way rotatable selector valve head (61) connected to an outlet (60) disposable peristaltic pump head connected to the outlet stator (10) of the rotating concentric hollow processing chamber (1).

Rotating Concentric Hollow Processing Chamber

The shape of the rotating concentric hollow processing chamber (1) is characterized by two parts, a spherical top part and a narrow funnel shaped bottom part. The top part of the chamber is a half sphere with a protruding hole at the very top (3) aligned with the center of the partial sphere. At the edges of the partial sphere (7), positioned between a quarter and halfway of the total height of the concentric processing chamber, preferably at a third, the bottom part begins, narrowing down into a funnel shape (6) that follows a concave arched curve with a second hole at the very bottom (4). Several holes (5) in the processing chamber wall are located closely above the bottom hole (4). The processing chamber edge (7) is characterized by a specific angle, which serves as a location for solids to aggregate and attach upon centrifugation (FIG. 9a). The very bottom of the rotating concentric processing chamber (30) is shaped as to fit a rotating socket (12) when mounted on the operating unit (80). The rotating socket (12) is connected to an electrical motor (17).

The processing chamber (1) possesses a hollow core (2) capable of receiving solutions of cells, biological samples or turbid biological suspensions. It is generally manufactured in medical grade plastic, such as, but not limited to; polyethylene terephthalate or polystyrene, and can have surface modifications appropriate for the application of interest.

The bottom of the processing chamber (4) is characterized by a central hole where the actionable plug (13) fits to the chamber and several side holes (5) that the plug (31) covers when engaged (32) that serve as an outlet for the liquid when the plug is disengaged (34), and the bottom of this chamber is engineered to fit and attach to an outlet stator (10).

The inlet stator (8) is located at the top of the rotating concentric hollow processing chamber (3) and partly inserted into it. It is engineered to hold the processing chamber (1) while still allowing for its rotation and for fluids to flow into it. The inlet stator (8) is characterized by two parts attached to each other. A bottom part (21) that encloses a waterproof bearing unit (22a) and rotary sealing units (23a) screwed on to a top part (20). The top part (20) of the stator (8) is characterized by an inlet tap connected to a screw-on male fitting (24) connected to the tubing (56). When pumped in, the liquid will enter the hollow concentric centrifugal chamber (2) via the inlet (9) on the top of the stator (20).

The outlet stator (10), located at the bottom of the concentric processing chamber (4), is engineered such that the processing chamber (1) can be held, rotated and fluids can flow out of it. This outlet (10) is characterized by a stator made of two parts screwed together. It is composed of a top part (25) that encloses two waterproof bearing units (22b) and rotary sealing units (23b) forming a liquid outlet chamber (27) that encloses the rotor bottom side holes (5) allowing the liquid to pass. The top (25) of the bottom stator (10) is held to the rotor by a snap ring (29) and tightened by the screw-on bottom part of the stator (26). The top (25) of the bottom stator (10) is characterized by an outlet tap connected to a screw-on male fitting (28) connected to the tubing (56).

At the center of the bottom stator (10), an actionable plug (13) fits into the concentric processing chamber (1). The actionable plug (13) can be engaged, acting as a liquid stopper (32), and disengaged, allowing the liquid to flow (34). When pumped out, the liquid will exit the rotating hollow concentric processing chamber (1) via the outlet (11)

on the bottom stator (10). The actionable plug (13) is a two-part element composed of a soft part of biocompatible rubber (31), fitting in the bottom of the rotating concentric hollow processing chamber (4), and a driving shaft (33) fitting into an actuator. The plug (13) is engaged (32) or disengaged (34) by means of an actuator and rotates with the processing chamber (1).

The rotating concentric hollow processing chamber (1) is rotatable about a central axis (14, 15) in both directions and rotatable about a perpendicular external axis (19) by means of the operating unit (80). The operating unit (80) can shift the concentric hollow processing chamber (1) from a vertical (14) to a horizontal position (15).

The specific shape of the rotating concentric hollow processing chamber (1) is necessary to perform the operations presented in the following section. The bottom part, shaped as a concave arched funnel, is critical as to allow liquid to accumulate rapidly at the fluid outlet (5) and be evacuated efficiently. Furthermore, the angle (6) at the outlet, when the actionable plug (13) is engaged (32), is not vertical. It allows, upon centrifugation, when the processing chamber (1) is vertical (14) to generate an upward force on the fluid displacing it at the processing chamber edge (7). The radius from the rotation axis (14) to the processing chamber edge (7) is sufficiently large to obtain a centrifugal force compatible with cellular processing at technically reasonable rotating speeds. The angle at the processing chamber edge (7) allows when centrifugation takes place for the solids to aggregate and remain attached. When oriented horizontally (15), the top half-sphere, allows for more volume to be stored in the processing chamber (1) and for the fluid to air interface in the processing chamber to be large enough with respect to cell culture standards.

Process or Operations

Automated manufacturing of cell-based therapeutic solutions is performed by means of the isolation and viral transformation of cells of interest from a biological fluid. The aforementioned manufacturing process is performed by sequential operations, such as filling the processing chamber, emptying the processing chamber, biological solid-matter separation from a suspension by centrifugation, suspension and mixing of biological solid matter in a liquid or reagent solution of interest, incubation of binding magnetic beads with a biological suspension, separation of magnetically tagged cells of interest from a biological suspension by magnetic bead separation using a magnetic array, transformation of cells of interest using a lentiviral vector or a RNA vector, modification of the solution volume, culture of cells of interest and expansion of these cells in the processing chamber.

In particular, another object of the present invention is to provide a process for the processing of biological fluids including biological solid separation, aggregate resuspension, reagents and/or cells incubation, magnetic separation of cells of interest and cell culture expansion in a rotating concentric hollow processing chamber (1) that can receive fluids and can be operated in multiple orientations in space by means of an operating unit (80) equipped with a set of reagents and bags part of a disposable kit (66) and capable of performing:

when oriented vertically (14) centrifugation in order to separate liquids from solids and volume adjustment;

when oriented horizontally (15) solid resuspension, magnetic beads magnetic attachment, solution incubation and mixing and volume adjustment;

and wherein the set of operations to perform said processing of biological fluids comprises a chained combination and/or repetition of procedures of volume adjustment and centrifugation when the rotating concentric hollow processing chamber (1) is vertical (14) and, low speed rotation, fast sequential clockwise and counterclockwise rotations, magnetic beads magnetic attachment, solution incubation and mixing when the rotating concentric hollow processing chamber (1) is horizontal (15).

In an embodiment, the invention provides for a process for biological solid separation which is performed by:

positioning the rotating concentric hollow processing chamber (1) vertically (14) by a rotation of the operating unit (80) and filling it with a biological suspension (100) that is then centrifuged by spinning the rotating concentric hollow processing chamber (1) along its axis (14) for a set time at a set speed to generate a centrifugal force, which results in the biological solids separating from the liquid and aggregating (102) on the edge (7) of the rotating concentric hollow processing chamber (1);

followed by stopping progressively the rotation of the rotating concentric hollow processing chamber (1), resulting in the liquid phase (101) flowing down and the solid phase (102) remaining attached to the edge (7) of the rotating concentric hollow processing chamber (1);

the resulting liquid phase (101) being pumped out at the outlet stator (10).

In another embodiment, the invention provides for a process for aggregate resuspension which is performed by:

positioning the rotating concentric hollow processing chamber (1) horizontally (15) by a rotation of the operating unit (80), and rotating the rotating concentric hollow processing chamber (1) about its horizontal axis (15) by series of fast sequential clockwise and counterclockwise rotations for a set time, and detaching the obtained aggregated solid (102) and suspending it in the liquid phase (106).

In yet another embodiment, the invention provides for a process for reagents and/or cells incubation, which is performed by:

positioning the rotating concentric hollow processing chamber (1) horizontally (15) by a rotation of the operating unit (80), mixing the biological suspension (106) in the processing chamber (1) with a reagent of interest and rotating the concentric processing chamber (1) about its central axis by a low speed rotation for a set time at a set temperature.

It is also another object of the invention to provide a process for magnetic separation of cells of interest, which is performed by:

incubating a biological suspension (103) with binding magnetic selection beads (104); orienting the rotating concentric hollow processing chamber (1) to a horizontal position (15) by a rotation of the operating unit (80); bringing the magnetic array (70) close to the edge (7) of the rotating concentric hollow processing chamber (1), resulting in the attraction of the magnetic beads (104);

rotating the operating unit (80) to position the rotating concentric hollow processing chamber (1) vertically (14) with the magnetic array (70) kept in close contact with the edge (7) of the rotating concentric hollow processing chamber (1), which results in the unwanted suspension (103) to flow to the bottom of the rotating concentric hollow processing chamber (1) and then be pumped out to a waste bag (62) while the cells of interest, attached to the magnetic beads (104) are magnetically resting at the edge (7); and retracting the magnetic array (70) to allow the magnetic beads (104) to freely flow.

It is still another object of the invention to provide a process for cell culture expansion, which is performed by:

having an homogeneous cell suspension (106) residing in cell culture medium inside the rotating concentric hollow processing chamber (1) oriented horizontally (15) by the action of the operating unit (80) performing low speed rotation so as to perform an incubation operation for a sufficient time;

after said sufficient time, the rotating concentric hollow processing chamber (1) is oriented vertically (14) by the action of the operating unit (80) and sampling is performed via a sampling port (64) in order to assess the cell culture (106) state; which in the case of a need for medium renewal a biological solid separation operation is performed with the old culture medium (101) being evacuated from the rotating concentric hollow processing chamber (1) and new cell culture medium is added (105), the procedure is followed by an aggregate resuspension followed by further incubation until cell count is satisfactory.

Filling and Emptying the Processing Chamber:

Filling the rotating concentric hollow processing chamber (1) can be performed in various ways.

1. The processing chamber (1) is oriented vertically (14) by means of the operating unit (80) with the inlet stator (8) facing up. The actionable plug (13) is engaged (32) blocking the chamber outlet holes (5). The peristaltic pump head (58) connected to the inlet stator (8) is activated in order for a reagent of interest to be pumped inside the processing chamber (2).

2. The processing chamber (1) is oriented horizontally (15) by means of the operating unit (80). The actionable plug (13) is engaged (32). The peristaltic pump head (58) connected to the inlet stator (8) is activated in order for a reagent of interest to be pumped inside the processing chamber (2).

3. The processing chamber (1) is oriented horizontally (15) by means of the operating unit (80). The actionable plug (13) is disengaged (34). The peristaltic pump head (60) connected to the outlet stator (10) is activated in order for a reagent of interest to be pumped inside the processing chamber (2). This case is particular as the part generally called the outlet stator (10) becomes an inlet stator.

Emptying the rotating concentric hollow processing chamber (1) can be performed in a single way. The processing chamber (1) is oriented vertically (14) by means of the operating unit (80) with the inlet stator (8) facing up. The actionable plug (13) is disengaged (34) uncovering the processing chamber outlet holes (5). The peristaltic pump head (60) connected to the outlet stator (10) is activated in order for the solution residing at the bottom of the processing chamber (6) to be pumped out of the processing chamber (2). The actionable plug (13) is engaged (32) again when the processing chamber (1) is empty.

Biological Solid Separation Operation

A biological solid separation operation (FIG. 9a) is typically performed as follows:

9a 1: The rotating concentric hollow processing chamber (1) is positioned vertically (14) by a rotation of the operating unit (80) and a solution of cells, biological fluid or turbid biological suspension (100) is loaded via the inlet (9) in the processing chamber (2) and flows to the bottom (6). The actionable plug (13) is engaged (32) forcing the fluid to stay in the processing chamber (2).

9*a* 2: The concentric hollow processing chamber (1) is rapidly spun about the vertical axis (14) to produce a centrifugal force for a set time. The suspension will flow towards the top part of the processing chamber and accumulate at the largest part (7) of the processing chamber (1). The biological solids will separate from the liquid and aggregate on the edge (7) of the concentric hollow processing chamber (1) forming a clear liquid phase (101) and a solid phase (102).

9*a* 3: The rotation of the concentric hollow centrifugal chamber (1) is slowly brought to a stop. The clear liquid phase (101) will flow down to the bottom (6) of the hollow chamber (2). The solid phase (102) will remain attached to the largest rotor part (7).

9*a* 4: The actionable plug (13) is disengaged (34) allowing the clear liquid to be pumped out from the concentric hollow processing chamber (2) via the outlet (11). The processing chamber (1) can be filled with a new liquid of interest for further washing or be filled with another volume of suspension to be separated.

Aggregate Resuspension Operation:

An aggregate resuspension operation (FIG. 9*c*) is typically performed as follows:

9*c* 1: The concentric hollow processing chamber (1), with centrifuged solids (102) attached to the processing chamber edge (7) post centrifugation, is brought to a horizontal position (15) by a rotation of the operating unit (80). A clear solution (105) which can be but is not limited to, cell culture medium or buffer, is loaded via the inlet (9) and flows to the processing chamber side (7). The processing chamber (1) is rotated following a series of fast sequential clockwise and counterclockwise rotations detaching the aggregated solid (102) and suspending it in the liquid phase (105).

9*c* 2: The rotation is brought to a stop, and an homogeneous cell suspension is obtained (106). The processing chamber (1) can be held horizontally (15) to further incubate the suspension or can be oriented vertically (14), for further processing by rotation of the operating unit (80)

Reagents and/or Cells Incubation Operation:

A reagent and/or cell incubation operation (FIG. 9*c* 2) is typically performed as follows:

9*c* 2: The rotating concentric hollow processing chamber (1) is positioned horizontally (15) by a rotation of the operating unit (80) and the biological suspension (106) present in the chamber is mixed with, but not limited to, a reagent of interest, a lentiviral vector or binding magnetic beads. The concentric processing chamber (1) is rotated about its central axis (15) by a slow rotation for a set time. Temperature can be adjusted as to satisfy incubation needs.

Magnetic Separation of Cells of Interest Operation

A magnetic separation of cells of interest operation (FIG. 9*b*) is typically performed as follows:

9*b* 1: A suspension of magnetic beads (104) for recognition of cellular features of interest is loaded via the inlet (9) inside the concentric hollow processing chamber (2) containing a solution of cells, biological samples or a turbid biological suspension (103) and flows to the bottom processing chamber (6).

9*b* 2: The rotating concentric hollow processing chamber (1) is brought to a horizontal position (15) by a rotation of the operating unit (80) and the solution is incubated by either a slow rotation or a slow clockwise and counterclockwise rotation about the processing chamber axis (15) for a set time at a set temperature. The rotation is brought to a stop and the magnetic beads (104) separate from the biological solution (103) by deposition.

9*b* 3: The magnetic array (70) is brought to the concentric processing chamber side (7), attracting and further separating the magnetic beads (104) from the biological solution (103).

9*b* 4: The operating unit (80) is rotated to position the rotating concentric hollow processing chamber (1) vertically (14) with the magnetic array (70) kept in close contact with the processing chamber edge (7). The unwanted suspension (103) flows to the bottom of the concentric processing chamber (6).

9*b* 5: The unwanted biological solution is evacuated from the concentric hollow centrifugal chamber (2) via the outlet (11). The cells of interest are still attached to the magnetic beads (104) by means of the magnetic array (70). The actionable plug (13) is engaged (32) and the magnetic array (70) can be retracted to release the magnetic beads or a liquid can be pumped into the concentric processing chamber (2) to further wash the attached cells (104).

Cell Culture Expansion Operation:

A cell culture expansion operation (FIG. 9*d*) is typically performed as follows:

9*d* 1: A homogeneous cell suspension (106) to be expanded resides in cell culture medium inside the rotating concentric hollow processing chamber (2).

9*d* 2: The rotating concentric hollow processing chamber (1) is oriented horizontally (15) by the action of the operating unit (80). The processing chamber is slowly rotated as to perform an incubation operation (FIG. 9*c* 2) at a set temperature.

9*d* 3: After a set time, the rotating concentric hollow processing chamber (1) is oriented vertically (14) by the action of the operating unit (80). The actionable plug (13) is disengaged (34) and sampling is performed via the sampling port (64) in order to assess the cell culture (106) state. If there is no need to renew the cell culture (106) medium the operating unit (80) reverts back to 9*d* 2.

Figure 9D:
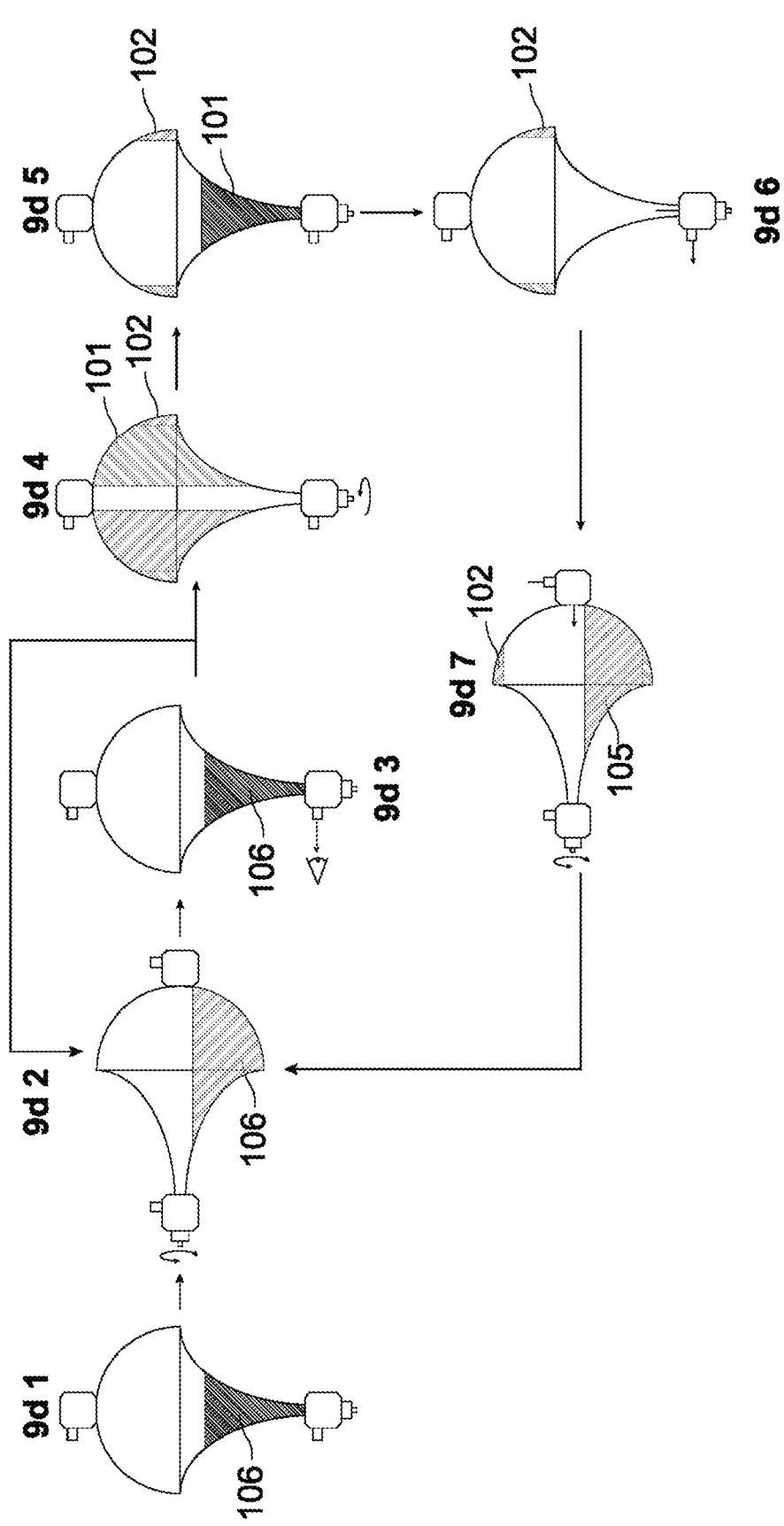
FIG. 9d is a flow diagram of a cell culture expansion operation.

9*d* 4 to 9*d* 6: The culture medium needs to be renewed. A biological solid separation operation is performed (FIG. 9*a*). The old culture medium (101) is evacuated (FIG. 9*d* 6) from the processing chamber (2) and new cell culture medium is added (105)

9*d* 7: An aggregate resuspension operation is performed (FIG. 9*c*) and the cell culture (106) is allowed to incubate (FIG. 9*c* 2) until cell count is satisfactory.

Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended Claims, and all changes which come within the meaning and range of equivalency are intended to be embraced therein.

Various references are cited throughout this specification, each of which is incorporated herein by reference in its entirety.

The foregoing description will be more fully understood with reference to the following Examples. Such Examples, are, however, exemplary of methods of practicing the present invention and are not intended to limit the scope of the invention.

Example 1: In one application, CD32+ cells are isolated, transformed and purified from white blood cells collected by apheresis to yield HIV-resistant hematopoietic stem cells. The reagents and the kit are prepared as follow: A bag of apheresis product (500 to 800 ml), a bag of phosphate buffer without calcium or magnesium (300 ml), a solution of lentivirus charged for the knockout of the CCR5 gene (50 to 100 ml), a solution of magnetic beads specifically targeting CD34+ cells (5 to 10 ml), a solution of high-glucose modified eagle cell culture growth medium (1.5 l), a waste bag (2 l) and a final product collection bag (100 ml). The operator orients the operating unit (80) for the reagent chamber (87) to face him using the operating unit orientation buttons (83). The reagent bags are placed in the reagent face chamber (87) and locked in place using straps. The tubing is fixed to the exit duct (85) in an orderly fashion, and the chamber is closed with the transparent plastic cover. The operator orients the operating unit (80) for the second face (91) to face him in order to install the inlet multiple-way rotary valve head (57) and peristaltic pump head (58). The operator ensures the tubing is clamped (84) to the face surface before orienting the rotor chamber (95) in front of him. The rotating concentric hollow processing chamber (1) is placed by first fitting the outlet stator (10) and the actionable plug (13) in the rotating socket (12). The inlet stator (8) is clipped into the socket at the top part of the rotor chamber (95). The safety cover glass (81) is locked to close the rotating chamber (95). The operator orients the operating unit (80) for the third face (92) to face him in order to install the outlet multiple-way rotary valve head (61) and peristaltic pump head (60). The operator fixes the tubing (56) in an orderly fashion in the output chamber entry duct (94) and rotates the operating unit (80) to place the waste (62) and final product bags (63) in their appropriate chamber (89) as well as the sampling tubing outlet (64) into its socket. The cell processing is launched by selecting the method on the operating unit (80) via the user interface (86) or via a remote terminal. The operator proceeds to a semi-automatized self-check to ensure optimal progression. The rotating concentric hollow processing chamber (1) is brought to a vertical position (14) by action of the operating unit (80). The lines are primed with phosphate buffer before loading the patient sample into the processing chamber (2). A biologic solid-matter separation operation (FIG. 9a) is performed, and the resulting liquid is pumped into the waste bag (62). Phosphate buffer is pumped into the processing chamber (2, 50 ml) and a biologic aggregate resuspension operation (FIG. 9c) is performed. The two previous operations are repeated twice to thoroughly wash the sample. An incubation operation (FIG. 9c2) with magnetic separation beads is then performed. A magnetic separation operation (FIG. 9b) is performed thrice, the two first with phosphate buffer (50 ml) the last with cell culture growth medium pumped into the processing chamber (2, 2 to 10 ml). An incubation operation (FIG. 9c 2) with the lentiviral vector is performed. A magnetic separation operation (FIG. 8b) is again performed thrice, the two first with phosphate buffer (50 ml) and the last with cell culture growth medium (50 ml). A cell culture expansion operation is performed until cell count reaches $10^9$ cells. A biologic solid-matter separation operation (FIG. 9a) is performed, and the resulting liquid is pumped into the waste bag (62). A biological aggregate resuspension operation (FIG. 9c) is performed, and all the solution is collected in the final product bag (63).

Example 2: This example illustrates frozen autologous stem cell preparation, for transplantation in the case of cancer treatment. A bag of selected patient stem cell (20 ml) is allowed to thaw. It is connected to a disposable kit (A variation from 66) composed of the following reagents: A bag of phosphate buffer without calcium or magnesium (300 ml), a solution of high-glucose modified eagle cell culture growth medium (1.5 l), a waste bag (2 l) and a final product collection bag (100 ml). The disposable kit (A variation from 66) is installed and the operating unit (80) is prepared to perform a process as presented in example 1. A biologic solid-matter separation operation (FIG. 9a) is performed, and the resulting liquid is pumped into the waste bag (62). Phosphate buffer is pumped into the processing chamber (2, 50 ml) and a biologic aggregate resuspension operation (FIG. 9c) is performed. The two previous operations are repeated twice to thoroughly wash the sample the last with cell culture growth medium (50 ml). A cell culture expansion operation is performed until cell count reaches $10^9$ cells. A biologic solid-matter separation operation (FIG. 9a) is performed, and the resulting liquid is pumped into the waste bag (62). A biological aggregate resuspension operation (FIG. 9c) is performed, and all the solution is collected in the final product bag (63).

The invention claimed is:

1. A rotating concentric hollow chamber configured for receiving fluids,
   the rotating concentric hollow chamber being adapted for being operated by an operating unit operated in multiple orientations in space for performing cell processing,
   the rotating concentric hollow chamber comprises two parts, a spherical top part and a narrow funnel shaped bottom part,
   wherein the top part is a half sphere with the round part facing up with a protruding hole at its very top, and
   wherein the narrow funnel shaped bottom part comprise a bottom hole at the very bottom of the funnel shape,
   wherein in that the rotating concentric hollow chamber is rotatable about a central axis in both directions and rotatable about an external axis perpendicular to said central axis, so that when the rotating concentric hollow chamber is operated by means of the operating unit, the rotating concentric hollow chamber is shifted from a vertical to a horizontal position, and
   wherein the narrow funnel shaped bottom part comprises a bottom edge of the half sphere positioned between a quarter and halfway of the total height of the rotating concentric hollow chamber forming a perpendicular angle with the bottom part of the rotating concentric hollow chamber which narrows down into a funnel shape that follows a concave arched curve with the bottom hole at its very bottom.

2. The rotating concentric hollow chamber of claim 1, wherein the bottom edge is characterized by a specific angle configured for serving as a location for solids to aggregate and attach upon centrifugation of said rotating concentric hollow chamber.

3. The rotating concentric hollow chamber of claim 1, wherein the rotating concentric hollow chamber is manufactured in medical grade plastic.

4. The rotating concentric hollow chamber of claim 3, wherein the medical grade plastic is chosen among polyethylene terephthalate or polystyrene.

5. The rotating concentric hollow chamber of claim 1, wherein the rotating concentric hollow chamber is fitted with an inlet stator at a top of the rotating concentric hollow chamber and an outlet stator at a bottom of the rotating concentric hollow chamber allowing liquids to be pumped in and out of the rotating concentric hollow chamber.

6. A single use disposable kit comprising a rotating concentric hollow chamber according to claim 1, wherein the rotating concentric hollow chamber is fitted with an inlet stator at a top of the rotating concentric hollow chamber and an outlet stator at a bottom of the rotating concentric hollow chamber allowing liquids to be pumped in and out of the rotating concentric hollow chamber, and wherein each of the inlet stator and the outlet stator are connected to an independent set composed of a disposable peristaltic pump head connected to a disposable multiple-way rotary selector valve head connected to several reagent or product pouches.

7. An automated apparatus suitable for the preparation of genetically transformed cells from biological fluids comprising the operating unit that is rotatable around its center about a horizontal axis, wherein the operating unit comprises the rotating concentric hollow chamber according to claim 1.

8. The automated apparatus of claim 7, wherein the apparatus further comprises a central axis shaft holding the operating unit providing support and electrical power.

9. The automated apparatus of claim 7, wherein the rotating concentric hollow chamber is fitted with an inlet stator at a top of the rotating concentric hollow chamber and an outlet stator at a bottom of the rotating concentric hollow chamber allowing liquids to be pumped in and out of the rotating concentric hollow chamber.

10. The automated apparatus of claim 9, wherein each of the inlet stator and the outlet stator are connected to an independent set composed of a disposable peristaltic pump head connected to a disposable multiple-way rotary selector valve head connected to several reagent or product pouches so as to form a disposable kit.

11. The automated apparatus of claim 7, wherein the operating unit is shaped as a hexagonal prism that possesses different functions for each of six operating unit faces and that can accommodate the rotating concentric hollow chamber in a rotor housing on one of the faces.

12. The automated apparatus of claim 11, wherein the six operating unit faces comprise:

two faces that are chambers configured for the storage of liquid bags that can be temperature controlled, one face which is the rotor housing that holds the rotating concentric hollow chamber and is equipped with an actionable magnetic array, one face that comprises a user interface as well as attachment points for a first peristaltic pump head and a first multiple-way rotary selector valve head, one face that comprises attachment points for a second peristaltic pump head and a second multiple-way rotary selector valve head and, one face that contains data input/output connectors, power connectors as well as venting for temperature control.

13. The automated apparatus of claim 12, wherein the actionable magnetic array consists in an arched shape designed to fit the bottom edge of the rotating concentric hollow chamber and further comprising one or more high magnetic field strength magnets.

* * * * *